United States Patent
Da Silva Barcia et al.

(10) Patent No.: US 11,701,612 B2
(45) Date of Patent: Jul. 18, 2023

(54) MULTI-STAGE PSA PROCESS TO REMOVE CONTAMINANT GASES FROM RAW METHANE STREAMS

(71) Applicant: SYSADVANCE—SISTEMAS DE ENGENHARIA S.A., Povoa de Varzim (PT)

(72) Inventors: Patrick Da Silva Barcia, Vila Do Conde (PT); Daniel Antonio Santos Silva Ferreira, Oporto (PT); Silvio Daniel Da Silva Carvalho Monteiro, Gondomar (PT)

(73) Assignee: SYSADVANCE—SISTEMAS DE ENGENHARIA S.A., Povoa de Varzim (PT)

( * ) Notice: Subject to any disclaimer, the term of this patent is extended or adjusted under 35 U.S.C. 154(b) by 475 days.

(21) Appl. No.: 15/734,803

(22) PCT Filed: Jun. 14, 2019

(86) PCT No.: PCT/IB2019/054996
§ 371 (c)(1),
(2) Date: Dec. 3, 2020

(87) PCT Pub. No.: WO2019/239381
PCT Pub. Date: Dec. 19, 2019

(65) Prior Publication Data
US 2021/0229027 A1 Jul. 29, 2021

(30) Foreign Application Priority Data
Jun. 14, 2018 (PT) .......................... 110787

(51) Int. Cl.
*B01D 53/047* (2006.01)
*B01D 51/10* (2006.01)
(Continued)

(52) U.S. Cl.
CPC ......... *B01D 53/0476* (2013.01); *B01D 51/10* (2013.01); *B01D 53/002* (2013.01);
(Continued)

(58) Field of Classification Search
CPC .. B01D 53/0476; B01D 51/10; B01D 53/002; B01D 2253/102; B01D 2253/116;
(Continued)

(56) References Cited

U.S. PATENT DOCUMENTS

| | | | | |
|---|---|---|---|---|
| 4,000,990 A | * | 1/1977 | Bingham | ........... B01D 53/0476 95/103 |
| 4,770,676 A | * | 9/1988 | Sircar | ................ B01D 53/0462 95/99 |

(Continued)

FOREIGN PATENT DOCUMENTS

WO 0056424 A1 9/2000

OTHER PUBLICATIONS

Carlos, A. "Biogas Upgrading by Pressure Swing Adsorption", Biofuel's Engineering Process Technology, 2011, pp. 1-21.
(Continued)

*Primary Examiner* — Frank M Lawrence, Jr.
(74) *Attorney, Agent, or Firm* — Lucas & Mercanti, LLP

(57) ABSTRACT

A multi-stage process to remove contaminant gases from raw methane streams is provided. The present technology is an innovative solution to recover and purify biogas by use of a process having at least two pressure swing adsorption stages. Taking advantage of the presence of carbon dioxide in the raw biogas streams, nitrogen and oxygen are bulky removed in the first stage, using selective adsorbents, and a nitrogen and oxygen-depleted intermediate stream is yielded to the second stage. The second stage employs an adsorbent or adsorbents to selectively remove carbon dioxide and trace amounts of remaining nitrogen and oxygen, thus producing
(Continued)

a purer methane stream that meets pipeline and natural gas specifications.

19 Claims, 3 Drawing Sheets

(51) Int. Cl.
*B01D 53/00* (2006.01)
*C07C 7/13* (2006.01)

(52) U.S. Cl.
CPC .......... *C07C 7/13* (2013.01); *B01D 2253/102* (2013.01); *B01D 2253/116* (2013.01); *B01D 2253/306* (2013.01); *B01D 2253/308* (2013.01); *B01D 2256/245* (2013.01); *B01D 2257/102* (2013.01); *B01D 2257/104* (2013.01); *B01D 2257/304* (2013.01); *B01D 2257/504* (2013.01); *B01D 2257/80* (2013.01); *B01D 2258/05* (2013.01); *B01D 2259/4062* (2013.01); *B01D 2259/40075* (2013.01); *B01D 2259/40079* (2013.01); *B01D 2259/40081* (2013.01); *B01D 2259/41* (2013.01); *B01D 2259/414* (2013.01)

(58) Field of Classification Search
CPC ........ B01D 2253/306; B01D 2253/308; B01D 2256/245; B01D 2257/102; B01D 2257/104; B01D 2257/304; B01D 2257/504; B01D 2257/80; B01D 2258/05; B01D 2259/40075; B01D 2259/40079; B01D 2259/40081; B01D 2259/4062; B01D 2259/41; B01D 2259/414; B01D 2101/02; B01D 46/00; B01D 51/00; B01D 2253/104; B01D 2253/106; B01D 2253/108; B01D 2253/204; B01D 2257/708; B01D 53/047; C07C 7/13
USPC .................... 95/96–98, 100, 103, 139, 141
See application file for complete search history.

(56) References Cited

U.S. PATENT DOCUMENTS

| | | | |
|---|---|---|---|
| 4,913,709 A * | 4/1990 | Kumar | B01D 53/0476 95/100 |
| 4,915,711 A | 4/1990 | Kumar | |
| 5,133,785 A * | 7/1992 | Kumar | B01D 53/0476 95/143 |
| 5,547,492 A * | 8/1996 | Cho | C01B 23/0052 95/122 |
| 5,989,316 A | 11/1999 | Kuznicki et al. | |
| 6,068,682 A | 5/2000 | Kuznicki et al. | |
| 6,197,092 B1 | 3/2001 | Butwell et al. | |
| 6,210,466 B1 | 4/2001 | Whysall et al. | |
| 6,315,817 B1 | 11/2001 | Butwell et al. | |
| 6,444,012 B1 | 9/2002 | Dolan et al. | |
| 6,631,626 B1 | 10/2003 | Hahn et al. | |
| 7,025,803 B2 | 4/2006 | Wascheck et al. | |
| 7,550,030 B2 * | 6/2009 | Kumar | B01D 53/0476 95/103 |
| 8,211,211 B1 * | 7/2012 | Knaebel | B01D 53/75 95/122 |
| 8,480,789 B2 | 7/2013 | Sorensen et al. | |
| 10,780,387 B1 * | 9/2020 | Siegel | B01D 53/053 |
| 2004/0099138 A1 | 5/2004 | Karode et al. | |
| 2016/0016866 A1 | 1/2016 | Kawashima et al. | |
| 2016/0097013 A1 | 4/2016 | Knaebel | |
| 2019/0275460 A1 * | 9/2019 | Zhong | B01D 53/0476 |

OTHER PUBLICATIONS

Santos, Monica et al., "Pressure Swing Adsorption for Biogas Upgrading. Effect of Recycling Streams in Pressure Swing Adsorption Design", Industrial & Engineering Chemistry Research, 2011, vol. 50, No. 2, pp. 974-985.

Cavenati, Simone et al., "Removal of Carbon Dioxide from Natural Gas by Vacuum Pressure Swing Adsorption", Energy & Fuels, 2006, vol. 20, No. 6, pp. 2648-2659.

International Search Report and Written Opinion for Corresponding International Application No. PCT/IB2019/054996 (14 Pages) (Dec. 5, 2019).

* cited by examiner

| STEP | 1 | 2 | 3 | 4 | 5 | 6 | 7 | 8 |
|---|---|---|---|---|---|---|---|---|
| ADSORBER 1 | FD | AD | | E↑ | BD | EV | PG | E↓ |
| ADSORBER 2 | BD | EV | PG | E↓ | FD | AD | | E↑ |

| STEP | 1 | 2 | 3 | 4 | 5 | 6 | 7 | 8 | 9 | 10 | 11 | 12 |
|---|---|---|---|---|---|---|---|---|---|---|---|---|
| ADSORBER 1 | | AD | | E1↑ | E2↑ | COD | EV | E1↓ | ID | E2↓ | ID | BF |
| ADSORBER 2 | EV | E1↓ | ID | E2↓ | ID | BF | | AD | | E1↑ | E2↑ | COD |
| ADSORBER 3 | E2↓ | ID | BF | | AD | | E1↑ | E2↑ | COD | EV | E1↓ | ID |
| ADSORBER 4 | E1↑ | E2↑ | COD | EV | E1↓ | ID | E2↓ | ID | BF | | AD | |

| STEP | 1 | 2 | 3 | 4 | 5 | 6 | 7 | 8 | 9 | 10 | 11 | 12 |
|---|---|---|---|---|---|---|---|---|---|---|---|---|
| ADSORBER 1 | | AD | COD | E1↑ | E2↑ | BD | EV | E1↓ | ID | E2↓ | BF | ID |
| ADSORBER 2 | EV | E1↓ | ID | E2↓ | BF | ID | | AD | | COD | E1↑ | E2↑ | BD |
| ADSORBER 3 | E2↓ | BF | ID | | AD | | COD | E1↑ | E2↑ | BD | EV | E1↓ | ID |
| ADSORBER 4 | E1↑ | E2↑ | BD | EV | E1↓ | ID | E2↓ | BF | ID | | AD | | COD |

MULTI-STAGE PSA PROCESS TO REMOVE CONTAMINANT GASES FROM RAW METHANE STREAMS

CROSS-REFERENCE TO RELATED APPLICATIONS

This application is a 371 of PCT/IB2019/054996, filed Jun. 14, 2019, which claims the benefit of Portuguese Patent Application No. 110787, filed Jun. 14, 2018, each of which are incorporated herein by reference.

TECHNICAL FIELD

The present application relates to a process to remove contaminant gases from raw methane streams.

BACKGROUND ART

Biogas from solid waste landfill is a very important and increasingly valued source of renewable methane. Typically, biogas from landfill contains, beyond methane, large amounts of carbon dioxide, nitrogen and oxygen and smaller amounts of other gaseous species such as nitrogen, oxygen, water vapor, hydrogen sulfide, hydrogen or many hydrocarbons and other organic compounds. Methane from biogas is commonly known as biomethane or renewable natural gas. Natural gas is a valuable commercial commodity as a combustible fuel for supplying energy and also as raw material in a significant number of relevant industrial processes. Also, if methane from an unrecovered landfill exhaust gas escapes into the atmosphere it will cause a serious environmental problem. Therefore, for several purposes, such as economic and ecological, it is of the utmost importance to recover and purify methane from landfill gas in such a manner as to meet the quality requirements and pipeline specifications.

Although carbon dioxide, the main contaminant, can be relatively easy to remove from raw biogas, the same is not applicable for the separation of nitrogen and oxygen from methane. Nonetheless, nitrogen must be separated since when its content exceeds a certain value in natural gas it has the effect of reducing the heat of combustion, which makes it less effective for heating or for generating power. Moreover, despite the fact that oxygen is typically not present in a significant quantity in natural gas, the presence of this contaminant is often observed in biogas from anaerobic digestion, landfill gas and coal bed gas. The presence of oxygen in the biomethane product has been progressively restrained for applications as Compressed Natural Gas (CNG) for vehicles or for biomethane injection in the natural gas grid. Both the CNG standards and the natural gas grid injection specifications are introducing stringent limits to the presence of $O_2$ [1].

Conventional methods of recovering methane from landfill exhaust gas have been developed and include fractional distillation processes, such as cryogenics, absorption, or gas separation processes, like pressure or temperature swing adsorption (PSA/TSA) or membranes. Concerning the challenging nitrogen and oxygen separation from methane, the cryogenic distillation has been the only process, so far, used to achieve this target and remove nitrogen from methane in natural gas. This technology is limited, however, to large scale plants, due to its expensive installation and high energy-consuming operation. Still, raw biogas from smaller-scale landfill reserves, that do not fit these criteria, is often left without being purified. For such scales, adsorption processes, such as PSA, can be especially well suited, due to its adaptability to different biogas mixture concentrations, low-cost and low-energy-consuming and easy-operation. The limitation, however, lies on the separation of nitrogen from methane. PSA units have been commercially used to separate a wide variety of biogas mixture concentrations, yet, limited by the ability to remove nitrogen and oxygen from the feed streams, usually delivers a biomethane that does not meet pipeline specifications, if nitrogen or oxygen concentrations in the biogas feed exceeds 3% and 1%, respectively.

The very few processes for the separation of nitrogen from methane from biogas streams containing carbon dioxide, nitrogen and oxygen can be listed without taking up large.

Kuznicki, Dolan, Butwell et al. from Engelhard Corporation developed a molecular sieve, Molecular Gate ETS-4, with improved selectivity between nitrogen and methane. In a series of patents (U.S. Pat. No. 6,068,682 issued May 30, 2000; U.S. Pat. No. 5,989,316 issued Nov. 23, 1999; U.S. Pat. No. 6,197,092 issued Mar. 6, 2001; WO Patent 00/56424 issued Mar. 8, 2000; U.S. Pat. No. 6,315,817 issued Nov. 13, 2001; and U.S. Pat. No. 6,444,012 issued Sep. 3, 2002), they exploit the special ability of this material to remove nitrogen and described a two-stage PSA process for treating biogas mixtures, among others. The first stage separates hydrocarbons and carbon dioxide from methane using a kinetic-driven adsorbent, and therefore the second stage improved biomethane concentration by reducing the nitrogen content, using ETS-4 molecular sieve. In the second stage, the separation is driven by the existing $CH_4/N_2$ selectivity, and the yielded product, methane, is obtained since it is the less-adsorbed component of the feed stream. Despite these promising features, the inventors describe only a separation from a methane-enriched natural gas stream (with 10% of $N_2$ and no $CO_2$), and that, in the end, does not meet the <3% $N_2$ pipeline specifications. Also, the inventors referred ETS-4 to require four parallel adsorbers to achieve smooth operation. Similarly, others developed and described PSA separations of nitrogen from methane, using special enhanced adsorbents, like titanium silicate molecular sieve (U.S. Pat. No. 6,631,626). Despite that, the so far described special enhanced adsorbents has the particularity of not having $CH_4/O_2$ selectivity, therefore increasing the oxygen content in their products stream and compromising the target of the grid biomethane specs.

Karode et al. from Air Liquide, also disclosed a membrane separation process for refining natural gas, especially exhaust gas from waste landfills (U.S. Patent 2004/0099138 issued May 27, 2004). The process disclosed includes a stage for removing moisture followed by a gas-liquid contact absorber to strip heavy hydrocarbon compounds in a primarily carbon dioxide by by-product stream. Then, the methane enriched gas from the absorber is separated in a membrane (or a series of membranes) separation unit which provides a purified biomethane product stream, while the carbon dioxide-enriched permeate is recycled to the absorber to washout the hydrocarbons. Despite the implicit ability of this process to treat and separate nitrogen present in landfill gas, the document does not refer that, nor does it present any results to support that assumption. A similar process was disclosed by Wascheck et al. from Air Liquide, in which the gas-liquid absorber was replaced by a pressure swing adsorption unit (U.S. Pat. No. 7,025,803 issued Apr. 11, 2006).

Membrane separation such as described usually involves two or more membranes in a series (multiple stages), to achieve a desirably biomethane product concentration. Multiple stages can generate potentially wasteful byproduct streams that further reduce the attractiveness of membrane separation to refine methane. Perhaps for these reasons, membrane separation processes have not therefore found great favor for commercially producing methane from landfill exhaust gas. In vision of that, more recently Sorensen et al. (U.S. Pat. No. 8,480,789 issued Jul. 9, 2013) developed and disclosed a process for separating and purifying a landfill gas stream combining a single-stage membrane unit followed by a pressure swing adsorption. Nonetheless, the adsorbent used in the PSA unit is referred to be Molecular Gate ETS-4, since it is the convenient way of removing nitrogen, as well as oxygen and remaining carbon dioxide, from an intermediate landfill stream, depleted carbon dioxide, delivered by the membrane-separation stage.

Knaebel (U.S. Patent 2016/0097013 issued Apr. 7, 2016), after describing an extensive background of five-adsorber PSA units, discloses a new PSA cycle capable of treat $N_2$-contaminated natural gas and yields a first product enriched in less-adsorbed component (such as nitrogen) followed by a second product enriched in more-strongly adsorbent components (such as methane). The process, described to use an activated carbon molecular sieve, runs, at high pressure, a 11-step cycle comprising an adsorption step, three equalization steps, a blowdown step followed by an evacuation step and also a purge under vacuum conditions, using the less-adsorbed first product stream to increase the $CH_4$ recovery. The patent simulation shown by Knaebel demonstrates a five-adsorber PSA able to reduce the content of $N_2$ down to 1.7% from a feed with 7.5% of $N_2$ and residual $CO_2$, with only 72% of recovery. This application is essentially adequate to $N_2$ rejection from natural gas, where the less adsorbed molecules are just nitrogen and methane, and where the $CO_2$ feed concentration is typically lower than 2%. Also, this technology does not mention the effect of the presence of other contaminants typically present in landfill gas such as oxygen.

In summary, despite the numerous applications, including PSA, to separate a wide variety of components that are present in landfill waste gas, mainly carbon dioxide and hydrocarbons, the separation of nitrogen and oxygen from methane still remains the limiting factor. Also, the few existing processes that attempt to fulfill this separation requires the combination of technologies in a multiple-stage operation, always very expensive and complex, and very often failing to meet the specifications, thus remaining unmarketable.

In contrast with the previously described documents, the present application discloses an innovative solution to recover and purify biogas, by use of an, at least, two-stage pressure swing adsorption (PSA), using commercially available adsorbents: molecular sieves to remove bulk nitrogen and oxygen from raw biogas streams in the first stage, yielding an intermediate nitrogen and oxygen-depleted stream to the second stage, that employs a molecular sieve to remove carbon dioxide and trace amounts of remaining nitrogen and oxygen, thus producing a purer biomethane stream that meets pipeline specifications.

The very few processes that tried to accomplish the nitrogen separation from biogas downstream the carbon dioxide removal, dealing with biomethane streams of 85-97% of methane balanced with nitrogen, reveals the binary separation methane-nitrogen to be harsh, resulting in a considerably methane loss (recoveries smaller than 60%).

The present technology deals with the nitrogen removal from raw biogas streams in a first stage, taking advantage of the presence of carbon dioxide. Carbon dioxide exhibits a strong adsorption capacity and high mass transfer rate onto the micropores of the selected molecular sieve, therefore pushing the less-adsorbed nitrogen and oxygen species out of the adsorber with the raffinate stream, while a methane and carbon dioxide enriched stream is delivered as extract product. The roll up effect created by the adsorption of the more strongly adsorbed molecule, $CO_2$, gives rise to a shaper mass front of $CH_4$, the second more adsorbed molecule, increasing the $CH_4$ recovery rate of the extract stream of the first separation stage.

SUMMARY

The present application relates to a multi-stage Pressure Swing Adsorption process to remove contaminant gases from raw methane streams, comprising at least two Pressure Swing Adsorption stages:
  First stage to remove Nitrogen and Oxygen, comprising the following steps:
    Feed ("FD");
    Adsorption ("AD");
    Equalization provided ("E1↑");
    Blowdown ("BD");
    Evacuation ("EV");
    Purge ("PG");
    Equalization received ("E↓"),
  wherein the first stage comprises at least one adsorbent, or mixture thereof, with strong affinity for carbon dioxide and methane;
  Second stage to remove Carbon Dioxide and residual Nitrogen and Oxygen comprising the following steps:
    Adsorption ("AD");
    Co-current depressurization ("COD");
    First equalization provided ("E1↑");
    Second equalization provided ("E2↑");
    Evacuation ("EV");
    First equalization received ("E1↓");
    Idle ("ID");
    Second equalization received ("E2↓");
    Idle ("ID");
  wherein the second stage comprises at least one adsorbent, or mixture thereof, with strong affinity for carbon dioxide.

In one embodiment the second stage further comprises a Blowdown ("BD") stage after the Second equalization provided ("E2↑") step and before the Evacuation ("EV") step.

In another embodiment the Co-current depressurization ("COD") step of the second stage occurs after the Second equalization provided ("E2↑") and before the Evacuation ("EV") step.

In yet another embodiment the second stage comprises a Backfill ("BF") stage after the Second equalization received ("E2↓") and before the second Idle ("ID") stage.

In one embodiment the second stage comprises a Backfill ("BF") stage after the second Idle ("ID") stage.

In one embodiment the process comprises a pre-treatment step before the first stage.

In another embodiment the first stage operates at a temperature between −50° C. and 120° C.

In yet another embodiment the operating pressure during the adsorption step in the first stage is between 60 kPa and 1500 kPa.

In one embodiment the purge to feed ratio varies between 0.3 to 0.9 depending on nitrogen feed stream content.

In another embodiment the operating desorption pressure in the evacuation step of the first stage ranges from 1 kPa to 100 kPa.

In yet another embodiment the intermediate biogas stream resultant of the first stage is pressurized between 200 kPa to 4.000 kPa and fed to the adsorption beds of the second stage.

In one embodiment the second stage operates at a temperature between −50° C. to 150° C.

In one embodiment the operating pressure during the adsorption step of the second stage is between 200 kPa and 4.000 kPa.

In another embodiment the operating desorption pressure in the evacuation step of the second stage is between 0.001 kPa and 100 kPa.

In one embodiment the adsorbents used in the first and second stage are selected from a list comprising zeolites, titanosilicates, metal-organic frameworks, activated carbons, carbon molecular sieves, alumina, silica gel, novel adsorbents like ionic liquid zeolites or other mesoporous materials with Si/Al-based.

In another embodiment the equalization occurs through the top.

In yet another embodiment the equalization occurs through the bottom.

In one embodiment the desorption in the evacuation step of the second stage occurs with purge.

In one embodiment the desorption in the evacuation step of the second stage occurs without purge.

General Description

As previously stated, biogas from solid waste landfills, beyond methane, comprises carbon dioxide, nitrogen, water vapor, hydrocarbons and other components in smaller quantities. The exact composition of the crude biogas stream varies from one landfill site to another and from the source (i.e. landfill, natural gas, digestor, coalbed methane gas, etc.). The raw biogas generally includes methane, carbon dioxide, nitrogen, oxygen and water vapor. In some instances, the raw biogas may also include hydrogen sulfide ($H_2S$), siloxanes and volatile organic compounds (VOCs), hydrogen or other hydrocarbons in smaller quantities.

Although pressure swing adsorption has been used to separate a wide variety of biogas mixture components, the limiting factor still remains in the separation of nitrogen and oxygen from methane. Conventional PSA processes to upgrade and purify raw biogas are able to remove carbon dioxide, oxygen, water vapor and hydrogen sulfide, and yield a biomethane product in which the contaminants concentration are under maximum specification limits. Exception occurs for nitrogen. Usually, such PSA processes, depending on the feed gas quality or biomethane product requirements, comprise one or more stages. The separation takes place exploiting the equilibrium and kinetic properties of the adsorbents used. The molecular sieves used retain more strongly the biogas contaminants, and a gas stream enriched in the less adsorbent component, methane, is delivered. Nitrogen, although slightly adsorbed, is commonly present in the yielded biomethane stream in the same concentration of the feed, if not higher.

The present application discloses a multi-stage PSA process to recover methane from raw biogas mixtures containing methane, carbon dioxide, oxygen and nitrogen, among others, thus producing a biomethane stream to meet pipeline specs. The present application discloses a process of, at least, two pressure swing adsorption stages. In one embodiment the process disclosed herein is preceded by a pre-treatment stage to remove adsorbent contaminants, such as $H_2S$, water vapor, etc. In the first stage PSA occurs the bulk removal of nitrogen and oxygen, and in the second stage PSA occurs the removal of carbon dioxide and trace removal of nitrogen and oxygen.

The novelty of this process consists on the fact that nitrogen and oxygen are removed from raw biogas stream in the first stage, taking advantage of the presence and significant amount of carbon dioxide (typically more than 30%) that exhibits a strong adsorption capacity and high mass transfer rate at the micropores of the selected molecular sieve. Such strong adsorption and fast kinetics pushes the weakly-adsorbed nitrogen and oxygen species out of the adsorption sites, yielding a nitrogen and oxygen-depleted biogas stream as extract product during desorption steps, while the undesired nitrogen and oxygen components are delivered as raffinate product during adsorption steps. At the first-stage PSA, the roll up effect created by the adsorption of the more strongly adsorbed molecule, $CO_2$, gives rise to a shaper mass transfer zone (MTZ) of $CH_4$, the second more adsorbed molecule. This sharper MTZ allows an easier separation between $CH_4$ and undesired $N_2$ and $O_2$, increasing the $CH_4$ recovery rate in the first separation stage.

Briefly, an overall description of process is provided below:

In one embodiment, the process comprises a pre-treatment stage, before the first-stage PSA.

The first-stage PSA comprises at least two adsorption beds filled with at least one selective adsorbent that is a molecular sieve with strong affinity to carbon dioxide and methane. Examples of these adsorbents are zeolites, titanosilicates, metal-organic frameworks, activated carbons, carbon molecular sieves, alumina, silica gel, novel adsorbents like ionic liquid zeolites (ILZ) or other mesoporous materials with Si/Al-based. The correct selection of the adequate molecular sieve for the first-stage PSA is of the utmost importance, since one should prefer adsorbents with both high $CH_4/N_2$ and $CO_2/N_2$ selectivity.

The first-stage PSA treats raw biogas feed at medium pressure and yields a raffinate product enriched in the less strongly adsorbed components, such as $N_2$, $O_2$ and others, and an extracted product enriched in the more strongly adsorbed components, such as $CH_4$, $CO_2$ and others. This extracted stream, methane-enriched and nitrogen-/oxygen-depleted is an intermediate biogas stream that is fed to the second-stage PSA.

The disclosed first-stage PSA undergoes a cyclic operation comprising the two main steps herein described:

The feed comprising the raw biogas passes through the adsorption beds containing the selective adsorber/molecular sieve with strong affinity for $CO_2$ and $CH_4$ molecules, pushing the non-adsorbed $N_2$ and $O_2$ out through the opposite side—raffinate product;

After this, vacuum is applied to the adsorption bed and a stream enriched in the adsorbed $CO_2$ and $CH_4$ is withdrawn—extract product. This intermediate biogas stream is then feed to the second-stage PSA.

The cycle process can comprise additional steps as is well known in the art.

The second stage comprises at least two adsorption beds to accomplish the separation between carbon dioxide and methane. In this second stage the separation is driven by the existing $CO_2/CH_4$ selectivity of the selected adsorbent or adsorbents that yields a product enriched in the less-adsorbed component, methane. Adsorbents should be selected from the group consisting of carbon molecular sieves, activated carbons, zeolites, titanosilicates, metal-organic frameworks, alumina, silica gel, novel adsorbents like ionic liquid zeolites (ILZ), or other mesoporous materials with Si/Al-based.

The intermediate biogas stream from the first-stage is pressurized and fed to the adsorption beds of the second stage PSA. There, the carbon dioxide, oxygen and part of the remaining nitrogen are adsorbed and removed from feed stream, thus enriching the biogas in the less adsorbed component, methane, that leaves as product.

A second-grade, methane-enriched stream, the recycling stream (with slightly more nitrogen content that of the product stream), is delivered and redirected to the first-stage feed in order to improve and slightly enrich the feed concentration in methane and reduce the levels of carbon dioxide, nitrogen and oxygen, also increasing methane recovery in more than 2%.

The disclosed second-stage PSA undergoes a cyclic operation comprising the following main steps:

The intermediate biogas stream coming from the first-stage passes through the adsorption beds containing a molecular sieve with high $CO_2/CH_4$ selectivity, thus removing the $CO_2$ and yielding a biomethane product through the opposite side—raffinate product.

A succession of intermediate steps with several equalizations between adsorbers, where part of gas that would be lost during desorption steps is used to pressurize the adsorbers that are preparing to produce, saving mechanical energy and increasing methane recovery. Also, during this, a second-grade, methane-enriched stream is recycled and redirected to the first-stage feed, also improving process performance.

After, the desorption steps take place, where adsorbed contaminants, $CO_2$, $O_2$ and $N_2$, are withdrawn from adsorption sites.

The cycle process can comprise additional steps as is well known in the art.

After the raw biogas is treated according to the present process, a final biogas stream is obtained, which consists primarily of methane (also known as "biomethane"). The final biomethane stream preferably meets a general standard, or level of quality requirements, and eligibility for common carrier natural gas pipelines.

With the herein disclosed process, the main goal of producing and delivering a purified biomethane in a substantially purified form in order to meet the pipeline specifications and requirements, can be attained.

BRIEF DESCRIPTION OF DRAWINGS

For easier understanding of this application, figures are attached in the annex that represent the preferred forms of implementation which nevertheless are not intended to limit the technique disclosed herein.

The illustrated embodiments are merely examples of the present invention and do not limit the scope of the invention.

The references shown in FIG. 1 are as follows:
1—crude biogas feed stream
2—filter
3—biogas blower
4—biogas heat exchanger
5—biogas feed stream
6—$H_2S$ guard bed
7—biogas feed stream
8—biogas feed stream
9—first stage feed pipeline
10—first stage intermediate biogas pipeline
11—first stage bottom equalization pipeline
12—first stage adsorption bed
13—first stage adsorption bed
14—first stage top equalization pipeline
15—first stage biogas purge pipeline
16—first stage biogas exhaust pipeline
17—biogas exhaust
18—biogas vacuum pump
19—intermediate biogas low pressure storage vessel
20—biogas compressor
21—intermediate biogas high pressure storage vessel
22—intermediate biogas stream
23—second stage bottom equalization pipeline
24—second stage feed pipeline
25—second stage exhaust pipeline
26—second stage adsorption bed
27—second stage adsorption bed
28—second stage adsorption bed
29—second stage adsorption bed
30—second stage top equalization pipeline
31—second stage biogas recycle pipeline
32—second stage biomethane pipeline
33—recycle stream/off-spec biomethane product
34—biogas vacuum pump
35—exhaust biogas
36—biomethane product
37—biomethane product storage vessel
38—biomethane product

DESCRIPTION OF THE EMBODIMENTS

Figure 1:
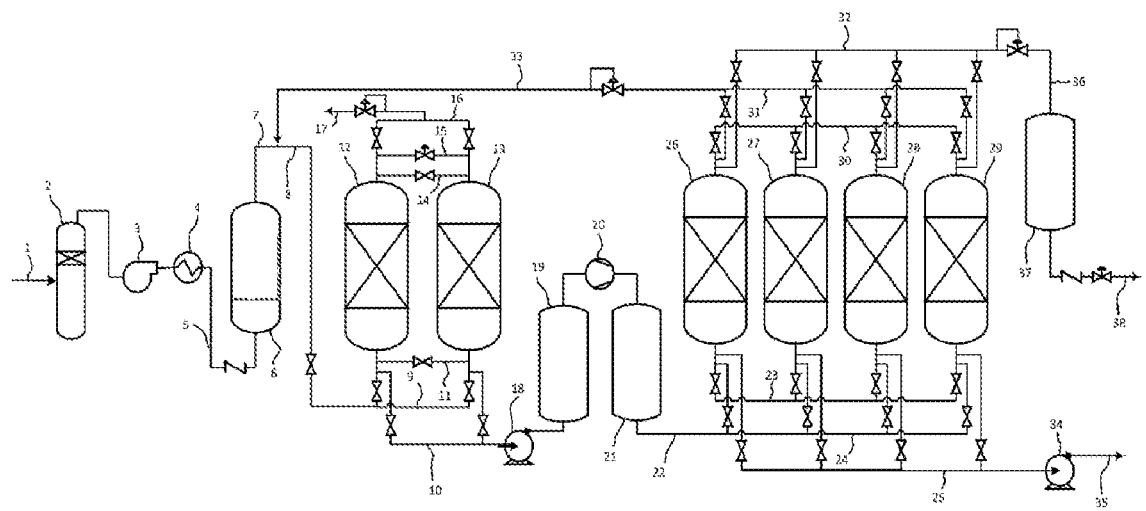
FIG. 1 is a diagram of the process herein disclosed to recover methane from biogas by use of a two-stage pressure swing adsorption, by removing bulk nitrogen and oxygen from raw landfill gas in the first stage, and carbon dioxide from methane in the second stage, thus yielding a pure biomethane stream. The process considers a pre-treatment stage.

Hereinafter, the process will be described in detail with reference to the annexed drawings. A number of preferred embodiments will be described, but they are not intended to limit the scope of this application. Various modifications may be made in the spirit and without departing from the scope of the technology.

The present application discloses a process comprising at least two PSA stages.

In one embodiment, the process comprises a pre-treatment stage, before the first-stage PSA, in order to reduce water level of raw biogas feed down to 5° C. of dew point, and $H_2S$ content down to 2 ppm. This pre-stage solution comprises a filter, or a series of filters, for water and particles removal, followed by a biogas blower and a heat exchanger that reduces the temperature of the feed stream down to 5°

C., thus removing moisture by condensation. The pre-stage also comprises an activated carbon adsorption filter of one or more vessels filled with an impregnated or non-impregnated activated carbon capable of removing hydrogen sulfide and other sulfur compounds.

The first-stage PSA runs for each adsorber a cycle comprising the following sequence of steps in a repeating order (FIG. 2):

- Feed ("FD"), where the adsorber is pressurized with feed stream up to the higher operating pressure. The gas flows upwards into the adsorber, while the more-strongly adsorbed components are retained and the gas-phase is enriched in the less-adsorbed components;
- Adsorption ("AD"), where the feed flows through the adsorber and the more-strongly adsorbed components are retained in the bed and a gas stream enriched in the less-strongly adsorbed component leaves the column through the opposite side. In one embodiment, during the adsorption step, a fraction of the less-strongly adsorbed stream is used to counter-currently purge the bed running purge ("PG") step at low operating pressure. The purge to feed (P/F) ratio varies between 0.3 to 0.9 depending on nitrogen feed stream content;
- Equalization provided ("E↑"), where the adsorber that has completed the adsorption step connects with the one that has been purged and the pressure between adsorbers is equalized. In this step, part of the gas that would be lost in the blowdown step is used to pressurize the other adsorber;
- Blowdown ("BD"), where the adsorber is counter-currently blowdown and some of the gas that is enriched in the more-strongly adsorbed components flows throw-out the adsorber and exits through feed end. The pressure in this step varies from the final pressure attained in equalization step to a final pressure near the low operating pressure;
- Evacuation ("EV"), the remaining gas that is enriched in the more-strongly adsorbed components is withdrawn from the adsorber, at low operating pressure, using a vacuum pump;
- Purge ("PG"), where a fraction of the less-strongly adsorbed components stream that is delivered during adsorption ("AD") is admitted to counter-currently pass through the bed at low operating pressure conditions. This gas forces the more-strongly adsorbed components to displace the adsorption sites of the molecular sieve, thus yielding a stream enriched in the more-strongly adsorbed components that is withdraw via vacuum pump.
- Equalization received ("E↓"), where the adsorber that has completed the evacuation and/or purge step connects with the one that has been adsorbing and the pressure between vessels is equalized. In this step, the adsorber is pressurized with gas provided by the other adsorber, naturally richer in methane (and poorer in nitrogen and oxygen) than the raw biogas feed stream.

The second-stage PSA runs, for each adsorber, a cycle comprising the following sequence of steps in a repeating order (FIG. 4):

- Adsorption ("AD"), where the adsorber is pressurized with feed stream to the higher operating pressure and the more-strongly adsorbed components are retained in the bed and a gas stream enriched in the less-strongly adsorbed component leaves the column through the top;
- Co-current depressurization ("COD"), where the adsorber is slowly co-currently depressurized and the depressurization gas is used as recycle stream that is fed to first stage;
- First equalization provided ("E1↑"), where the adsorber that has completed the co-current depressurization step connects with the one that has been idle after completed first equalization received step and the pressure between vessels is equalized;
- Second equalization provided ("E2↑"), where the adsorber that has completed the first equalization provided step connects with the one that has been evacuating and the pressure between vessels is equalized;
- Evacuation ("EV"), follows the blowdown step, the remaining gas that is enriched in the more-strongly adsorbed components is withdrawn from the adsorber through the feed end, at low operating pressure, using a vacuum pump;
- First equalization received ("E1↓"), where the adsorber that has completed the evacuation step connects with the one that has completed first equalization provided step and the pressure between vessels is equalized;
- Idle ("ID"), where the adsorber is on idle;
- Second equalization received ("E2↓"), where the adsorber that has been idle, after completed the first equalization received step, connects with the one that has completed co-current depressurization step and the pressure between vessels is equalized;
- Backfill ("BF"), where the adsorber that has completed the second equalization received step counter-currently receives part of the gas that leaves the adsorber that is under adsorption step;
- Idle ("ID"), where the adsorber is on idle.

In one embodiment, the second stage further comprises a Blowdown ("BD") stage, where the adsorber is counter-currently blowdown and a stream enriched in the more-strongly adsorbed components flows throw-out the adsorber through the feed end, which occurs after the Second equalization provided ("E2↑") and before the Evacuation ("EV").

In one embodiment, the second stage Co-current depressurization ("COD") step, of the second stage, occurs after the Second equalization provided ("E2↑") and before the Evacuation ("EV") step.

In another embodiment, the second stage comprises a Backfill ("BF") stage after the Second equalization received ("E2↓") and before the second Idle ("ID") stage.

In yet another embodiment, the second stage comprises a Backfill ("BF") stage after the second Idle ("ID") stage.

Figure 3:
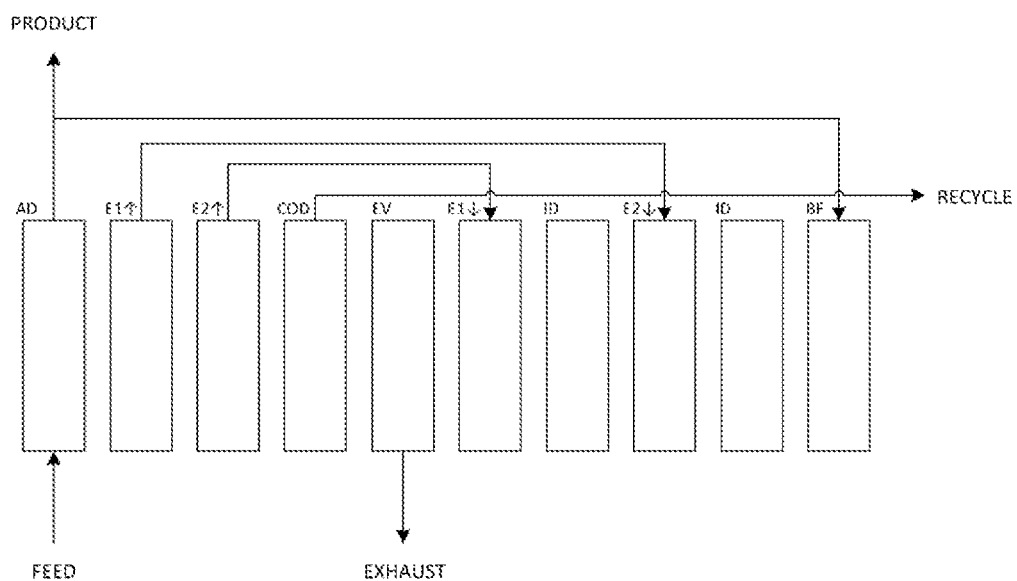
FIG. 3 is an illustration of one of proposed embodiments of second-stage PSA steps.

The previous embodiments form the following second-stage PSA sequence of steps in a repeating order (FIG. 3):

- Adsorption ("AD"), where the adsorber is pressurized with feed stream to the higher operating pressure, and the more-strongly adsorbed components are retained in the bed and a gas stream enriched in the less-strongly adsorbed component leaves the column through the top;
- First equalization provided ("E1↑"), where the adsorber that has completed the adsorption step connects with the one that has completed the first equalization received step and the pressure between vessels is equalized;
- Second equalization provided ("E2↑"), where the adsorber that has completed the first equalization provided step connects with the one that has been evacuating and the pressure between vessels is equalized;
- Co-current depressurization ("COD"), where the adsorber that has completed the second equalization provided step is co-currently depressurized, and being the depressurization gas used as recycle stream that is fed to the first stage;

Evacuation ("EV"), where the adsorber is counter-currently evacuated, using a vacuum pump, and a stream enriched in the more-strongly adsorbed components is withdrawn from the adsorber, at low operating pressure;

First equalization received ("E1↓"), where the adsorber that has completed the evacuation step connects with the one that has completed first equalization provided step and the pressure between vessels is equalized;

Idle ("ID"), where the adsorber is on idle;

Second equalization received ("E2↓"), where the adsorber that has been idle after completed the first equalization received step connects with the one that has completed adsorption step and the pressure between vessels is equalized;

Idle ("ID"), where the adsorber is again on idle;

Backfill ("BF"), where the adsorber that has completed the second equalization received step counter-currently receives part of the gas that leaves the adsorber that is under adsorption step.

The first stage operates at a temperature between −50° C. and 120° C. In a preferred embodiment the first stage occurs at a temperature between from 0 to 70° C.

The operating pressure during the adsorption step in the first stage is between ca. 60 kPa and 1500 kPa. In a preferred embodiment the pressure is between 80 kPa and 400 kPa. In a more preferred embodiment the pressure is between 100 to 150 kPa.

The operating desorption pressure in the evacuation step of the first stage ranges from 1 kPa to 100 kPa. In a preferred embodiment the pressure is between 10 kPa and 80 kPa. In a more preferred embodiment the pressure is between 20 and 60 kPa.

The intermediate biogas stream resultant of the first stage is pressurized between ca. 200 kPa to 4.000 kPa and fed to the adsorption beds of the second-stage PSA. In a preferred embodiment it is pressurized between 500 kPa and 1.000 kPa. In a more preferred embodiment it is pressurized between 600 to 900 kPa.

The second stage operates at a temperature of −50° C. to 150° C. In a preferred embodiment the temperature is between 10 and 80° C.

The operating pressure during the adsorption step of the second stage is between ca. 200 kPa and 4.000 kPa. In a preferred embodiment the pressure is between 500 kPa and 1.000 kPa. In a more preferred embodiment the pressure ranges from 600 to 900 kPa.

The operating desorption pressure in the evacuation step of the second stage is between 0.001 kPa and 100 kPa. In one preferred embodiment the pressure ranges from 0.01 kPa to 20 kPa. In a more preferred embodiment the pressure ranges from 0.1 to 10 kPa.

The adsorbers in the first and second stage are filled with at least one selective adsorbent, or mixture thereof, that is a molecular sieve with strong affinity to carbon dioxide and methane. Adsorbents should be selected from the group consisting of carbon molecular sieves, activated carbons, zeolites, titanosilicates, metal-organic frameworks, alumina, silica gel, novel adsorbents like ionic liquid zeolites (ILZ) or other mesoporous materials with Si/Al-based.

The first stage and second stage comprise at least two adsorption beds each. In one embodiment, the second stage comprises four adsorption beds.

An overview of the process of the present technology can be described by referring to FIG. 1.

In one embodiment, as shown, the process comprises a pre-treatment stage. Raw biogas feed stream (1) enters the pre-treatment stage that comprises a filter or a series particle filters (2), a biogas blower (3), a heat exchanger (4) that lowers the temperature of the feed stream down to 5° C. and the condensed water is removed, and a hydrogen sulfide guard bed (6). The hydrogen sulfide guard bed (6) is filled with activated carbon that lowers the $H_2S$ content down to ppm level. The biogas feed current (7) that exits this pre-treatment stage has less than 2 ppm of $H_2S$ and less than 9000 ppm of $H_2O$.

The raw biogas feed stream (7) typically contains up to 12 mol % of $N_2$, 5 mol % of $O_2$, 35 mol % of $CO_2$ and 48 mol % of $CH_4$, and can be combined with the recycling stream (31) from the co-current depressurization of second-stage PSA, typically containing 91-97% $CH_4$, 0.2-2.0% $CO_2$, 3.0-6.0% $N_2$, 0.2-1.0% $O_2$, thus generating the stream (8) slightly methane-enriched that is fed to the first-stage PSA.

Figure 2:
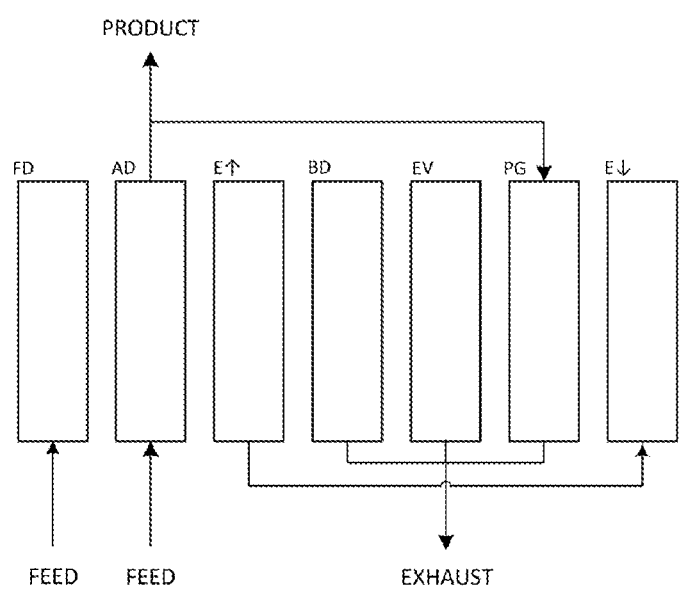
FIG. 2 is an illustration of the proposed first-stage PSA steps.
Figures 5, 6, 7, 8:
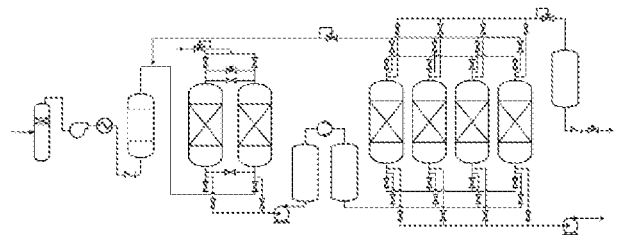
FIG. 5 is a schematic diagram of the first-stage PSA steps sequence.
FIG. 6 is a schematic diagram of the second-stage PSA steps sequence.
FIG. 7 is a schematic diagram of another embodiment of the second-stage PSA steps sequence.
FIG. 8 is a diagram of the process herein disclosed to recover methane from biogas by use of a two-stage pressure swing adsorption.

The cycle steps of first-stage PSA occur as previously described (FIG. 2 and FIG. 5). In one embodiment the first-stage PSA operates at a temperature of −50° C. to 120° C., more preferably from 0 to 70° C.

The adsorbent, or a combination of adsorbents, selected are nitrogen-selective molecular sieves, from the group consisting of carbon molecular sieves, activated carbons, zeolites, titanosilicates, metal-organic frameworks, alumina, silica gel, novel adsorbents like ionic liquid zeolites (ILZ) or other mesoporous materials with Si/Al-based.

The adsorber (12) is pressurized with a biogas feed stream through line (9). The pressure during the adsorption is from ca. 60 kPa to 1500 kPa, preferably between 80 kPa and 400 kPa, and more preferably from 100 to 150 kPa.

The gas flows upwards into the adsorber, while the more-strongly adsorbed components are retained and the gas-phase is enriched in the less-adsorbed components. Adsorption step takes place, where biogas feed flows through the adsorber (12) and the more-strongly adsorbed components are retained in the bed and a gas stream enriched in the less-strongly adsorbed component leaves the column through line (16). During this, a fraction of the less-strongly adsorbed stream is used to counter-currently purge the adsorber (13) through the line (15).

After the adsorption step is completed, adsorbers are connected through line (11), at the bottom, and the pressure between adsorbers is equalized. In another embodiment, adsorbers are connected through line (14), at the top, and the pressure between adsorbers is equalized.

After the equalization step, the adsorber (12) is counter-currently blowdown and evacuated through exhaust line (10) using a vacuum pump (18). The desorption pressure ranges from 1 kPa to 100 kPa, preferably from 10 kPa to 80 kPa, and more preferably from 20 to 60 kPa.

An intermediate biogas stream, nitrogen and oxygen depleted, is then collected and stored in vessel (19). While adsorber (12) is evacuating, part of the less-strongly adsorbed stream exiting the adsorber (13) through top is admitted to counter-currently purge the adsorber (12). The part of raffinate stream used to purge the adsorber (12) depends on the nitrogen content of the feed stream varying, the herein designated purge to feed (P/F) ratio, between 0.3 to 0.9. Afterwards, both adsorbers (12) and (13) are connected through the line (11) and their pressure equalized. In another embodiment, adsorbers are connected through the line (14) and their pressure is equalized.

The biogas intermediate stream is stored in vessel (19) and pressurized in biogas compressor (20) before fed to the second-stage PSA through line (22).

The intermediate biogas stream is pressurized from ca. 200 kPa to 4.000 kPa, preferably between 500 kPa and 1.000 kPa, and more preferably from 600 to 900 kPa, and fed to the adsorption beds of the second-stage PSA.

Figure 4:
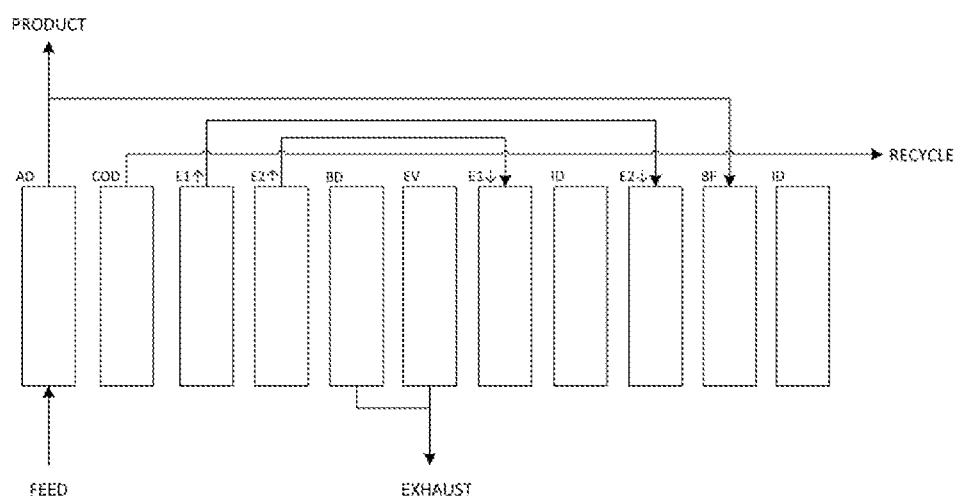
FIG. 4 is an illustration of another of proposed embodiments of second-stage PSA steps.

The process steps of this second-stage were previously described (FIG. 4 and FIG. 7). The second-stage PSA operates at a temperature of −50° C. to 150° C., more preferably from 10 to 80° C.

Adsorbent or the combination of adsorbents selected has high $CO_2/CH_4$ selectivity, and should be selected from the group consisting of carbon molecular sieves, activated carbons, zeolites, titanosilicates, metal-organic frameworks, alumina, silica gel, novel adsorbents like ionic liquid zeolites (ILZ) or other mesoporous materials with Si/Al-based.

The adsorber (26) is pressurized with intermediate biogas stream from first-stage and the gas flows upwards into the adsorber, while the more-strongly adsorbed components are retained and the gas-phase is enriched in the less-adsorbed component, that leaves the adsorber through the line (32) and is stored in vessel (36). The pressure during the adsorption is from ca. 200 kPa to 4.000 kPa, preferably between 500 kPa and 1.000 kPa, and more preferably from 600 to 900 kPa.

After completing the adsorption step, the feed end is closed and the adsorber (26) co-currently depressurizes through line (31), delivering a second-grade methane-enriched stream to be recycled and fed to the first-stage PSA, that is mixed with biogas coming from feed stream (7). This enriches the feed stream (8) concentration in methane and reduces the levels of carbon dioxide, nitrogen and oxygen.

After, the adsorbers (26) and (27) are connected through line (30) and pressure between them equalized. In another embodiment adsorbers are connected through line (23) and pressure between them equalized. After completing the first equalization provided step, the adsorber (26) and adsorber (29) are connected through line (30) and pressure equalized. In another embodiment the adsorbers (26) and (29) are connected through line (23) and pressure between them equalized.

After, the adsorber (26) is counter-currently blowdown and evacuated through exhaust line (25) using a vacuum pump (34) and an exhaust product (35) enriched in the more-strongly adsorbed components delivered. In one embodiment the desorption step occurs with purge, through pipeline (31). In another embodiment the desorption occurs without purge. The desorption pressure ranges from 0.001 kPa to 100 kPa, preferably from 0.01 kPa to 20 kPa, and more preferably from 0.1 to 10 kPa.

Afterwards, two equalization steps take place. First, adsorber (26) and (28) are connected through pipeline (30) and pressure equalized, and second, after an idle step, adsorber (26) and (27) are connected through pipe (30) and pressure equalized. In another embodiment, both equalization steps are made connecting the adsorbers through line (23). After a step in which adsorber (26) is on idle, backfill step takes place. During this step, immediately prior to adsorption, the adsorber (26) counter-currently receives part of the gas produced and stored in vessel (37) through line (32).

In another embodiment, the process steps of the second-stage, previously described (FIG. 3 and FIG. 6) can be detailed as follows. The second-stage PSA operates at a temperature of −50° C. to 150° C., more preferably from 10 to 80° C. The adsorbent, or the combination of adsorbents, selected has high $CO_2/CH_4$ selectivity, and should be selected from the group consisting of carbon molecular sieves, activated carbons, zeolites, titanosilicates, metal-organic frameworks, alumina, silica gel, novel adsorbents like ionic liquid zeolites (ILZ) or other mesoporous materials with Si/Al-based.

The adsorber (26) is pressurized with intermediate biogas stream from first-stage and the gas flows upwards into the adsorber, while the more-strongly adsorbed components are retained and the gas-phase is enriched in the less-adsorbed component, that leaves the adsorber through the line (32) and is stored in vessel (36). The pressure during the adsorption is from ca. 200 kPa to 4.000 kPa, preferably between 500 kPa and 1.000 kPa, and more preferably from 600 to 900 kPa.

After completing the adsorption step, the adsorbers (26) and (27) are connected through line (30) and pressure between them is equalized. In another embodiment adsorbers are connected through line (23), at the bottom, and pressure between them equalized. After completing the first equalization provided step, the adsorber (26) and adsorber (29) are connected through line (30), at the top, and pressure equalized. In another embodiment the adsorbers (26) and (29) are connected through line (23) and pressure between them equalized.

After, the adsorber (26) co-currently depressurizes through line (31), delivering a second-grade methane-enriched stream to be recycled and fed to the first-stage PSA, that is mixed with biogas coming from the feed stream (7). This improves and slightly enriches the feed stream (8) concentration in methane and reduces the levels of carbon dioxide, nitrogen and oxygen.

After, the adsorber (26) is counter-currently blowdown and evacuated through exhaust line (25) using a vacuum pump (34) and an exhaust product (35) enriched in the more-strongly adsorbed components delivered. In one embodiment the desorption step occurs with purge, through pipeline (31). In another embodiment the desorption occurs without purge. The desorption pressure ranges from 0.001 kPa to 100 kPa, preferably from 0.01 kPa to 20 kPa, and more preferably from 0.1 to 10 kPa.

Afterwards, two equalization steps take place. First, adsorber (26) and (28) are connected through pipeline (30) and pressure equalized, and second, after an idle step, adsorber (26) and (27) are connected through pipe (30) and pressure equalized. In another embodiment, both equalization steps are made connecting the adsorbers through line (23).

After a step in which adsorber (26) is on idle, backfill step takes place. During this step, immediately prior to adsorption, the adsorber (26) counter-currently receives part of the gas produced and stored in vessel (37) through line (32).

In preferred embodiments, the final biomethane gas contains no more than 0.5 mol % of $CO_2$, less than 3 mol % of $N_2$, less than 0.2 mol % of $O_2$ and less than 2 ppm of $H_2S$, in a dry basis.

Although the preferred embodiments of the present invention have been disclosed for illustrative purposes, those skilled in the art will appreciate that various modifications, additions and substitutions are possible, without departing from the scope of the invention. Therefore, the present technology is not limited to the above-described embodiments, but the present invention is defined by the claims which follow, along with their full scope of equivalents.

EXAMPLES

Example 1

In this example, the removal of contaminant gases from a landfill biogas stream according to one embodiment of the present application is simulated computationally. According to the simulation, a biomethane stream of 174 m³/h with 96.8% of $CH_4$, 0.1% of $CO_2$, 3.0% of $N_2$ and 0.1% of $O_2$ is recovered from a raw landfill biogas stream containing 48.0% of $CH_4$, 35.0% of $CO_2$, 12.0% of $N_2$ and 5.0% of $O_2$. The flow rate of the raw landfill biogas stream is 530 m³/h.

In this embodiment, the first-stage PSA comprises two adsorption beds, packed with activated carbon with 900-1200 m²/g of total surface area (B.E.T.), running the cyclic sequence of steps schematized in FIG. 5. The second-stage PSA comprises four adsorption beds, packed with a carbon molecular sieve with pore width of 3-7 Å, running the cyclic sequence of steps schematized in FIG. 7.

The results obtained are listed in Table 1. This table resumes the composition as well as the pressure and temperature conditions of each crucial stream of the process illustrated in FIG. 1.

TABLE 1

|  | 1 | 7 | 8 | 17 | 19 | 21 | 35 | 38 | 33 |
|---|---|---|---|---|---|---|---|---|---|
| CH4, % | 48.0 | 48.0 | 49.4 | 37.8 | 55.7 | 55.7 | 1.9 | 96.8 | 95.1 |
| CO2, % | 35.0 | 35.0 | 34.0 | 23.8 | 39.6 | 39.6 | 91.3 | 0.1 | 1.4 |
| N2, % | 12.0 | 12.0 | 11.7 | 27.4 | 3.2 | 3.2 | 3.5 | 3.0 | 3.1 |
| O2, % | 5.0 | 5.0 | 4.9 | 11.0 | 1.5 | 1.5 | 3.3 | 0.1 | 0.4 |
| H2S, ppm | 1500 | 0 | 0 | 0 | 0 | 0 | 0 | 0 | 0 |
| H2O, ppm | 28000 | 9600 | 9166 | 117 | 11300 | 900 | 2059 | 39 | 43 |
| P/kPa | 101 | 120 | 134 | 128 | 102 | 850 | 1 | 750 | 600 |
| T/° C. | 23 | 23 | 40 | 30 | 15 | 45 | 15 | 35 | 30 |
| Flow/ m3·h⁻¹ | 530 | 500 | 515 | 182 | 333 | 333 | 144 | 174 | 15 |

Example 2

In this example, the removal of contaminant gases from a landfill biogas stream according to one embodiment of the present application is simulated computationally. According to the simulation, a biomethane stream of 222 m³/h with 96.9% of $CH_4$, 0.1% of $CO_2$, 2.9% of $N_2$ and 0.1% of $O_2$ is recovered from a raw landfill biogas stream containing 50.0% of $CH_4$, 39.0% of $CO_2$, 8.0% of $N_2$ and 3.0% of $O_2$. The flow rate of the raw landfill biogas stream is 530 m³/h.

In this embodiment, the first-stage PSA comprises two adsorption beds, packed with activated carbon with 900-1200 m²/g of total surface area (B.E.T.), running the cyclic sequence of steps schematized in FIG. 5. The second-stage PSA comprises four adsorption beds, packed with a carbon molecular sieve with pore width of 3-7 Å, running the cyclic sequence of steps schematized in FIG. 7.

The results obtained are listed in Table 2. This table resumes the composition as well as the pressure and temperature conditions of each crucial stream of the process illustrated in FIG. 1.

TABLE 2

|  | 1 | 7 | 8 | 17 | 19 | 21 | 35 | 38 | 33 |
|---|---|---|---|---|---|---|---|---|---|
| CH4, % | 50.0 | 50.0 | 51.7 | 33.4 | 55.9 | 55.9 | 1.6 | 96.9 | 95.3 |
| CO2, % | 39.0 | 39.0 | 37.6 | 28.1 | 39.7 | 39.7 | 92.2 | 0.1 | 1.3 |
| N2, % | 8.0 | 8.0 | 7.8 | 28.6 | 3.1 | 3.1 | 3.4 | 2.9 | 3.0 |
| O2, % | 3.0 | 3.0 | 2.9 | 10.0 | 1.3 | 1.3 | 2.9 | 0.1 | 0.4 |
| H2S, ppm | 1500 | 0 | 0 | 0 | 0 | 0 | 0 | 0 | 0 |
| H2O, ppm | 28000 | 9600 | 9166 | 117 | 11300 | 900 | 2059 | 39 | 43 |
| P/kPa | 101 | 120 | 139 | 128 | 102 | 850 | 1 | 750 | 600 |
| T/° C. | 23 | 23 | 40 | 30 | 15 | 45 | 15 | 35 | 30 |
| Flow/ m3·h⁻¹ | 530 | 500 | 520 | 96 | 424 | 424 | 182 | 222 | 20 |

Example 3

In this example, the removal of contaminant gases from a digestor gas stream according to one embodiment of the present application is simulated computationally. According to the simulation, a biomethane stream of 206 m³/h with 98.9% of $CH_4$, 0.2% of $CO_2$ and 0.9% of $N_2$ is recovered from a raw landfill biogas stream containing 52.0% of $CH_4$, 44.0% of $CO_2$, 3.0% of $N_2$ and 1.0% of $O_2$. The flow rate of the raw landfill biogas stream is 530 m³/h.

In this embodiment, the first-stage PSA comprises two adsorption beds, packed with activated carbon with 900-1200 m²/g of total surface area (B.E.T.), running the cyclic sequence of steps schematized in FIG. 5. The second-stage PSA comprises four adsorption beds, packed with a carbon molecular sieve with pore width of 3-7 Å, running the cyclic sequence of steps schematized in FIG. 6.

The results obtained are listed in Table 3. This table resumes the composition as well as the pressure and temperature conditions of each crucial stream of the process illustrated in FIG. 1.

TABLE 3

|  | 1 | 7 | 8 | 17 | 19 | 21 | 35 | 38 | 33 |
|---|---|---|---|---|---|---|---|---|---|
| CH4, % | 52.0 | 52.0 | 53.1 | 56.0 | 52.4 | 52.4 | 0.7 | 98.9 | 90.1 |
| CO2, % | 44.0 | 44.0 | 43.0 | 29.2 | 46.2 | 46.2 | 97.4 | 0.2 | 8.2 |
| N2, % | 3.0 | 3.0 | 2.9 | 11.3 | 1.0 | 1.0 | 1.1 | 0.9 | 1.1 |
| O2, % | 1.0 | 1.0 | 1.0 | 3.5 | 0.4 | 0.4 | 0.8 | 0.0 | 0.6 |
| H2S, ppm | 1500 | 0 | 0 | 0 | 0 | 0 | 0 | 0 | 0 |
| H2O, ppm | 28000 | 9600 | 9166 | 117 | 11300 | 900 | 2059 | 39 | 43 |
| P/kPa | 101 | 130 | 130 | 128 | 102 | 850 | 1 | 750 | 150 |
| T/° C. | 23 | 23 | 40 | 30 | 15 | 45 | 15 | 35 | 30 |
| Flow/ m3·h⁻¹ | 530 | 500 | 515 | 98 | 417 | 417 | 196 | 206 | 15 |

REFERENCES

[1] SOUTHERN CALIFORNIA GAS COMPANY Revised CAL. P.U.C. SHEET NO. 47193-G.

The invention claimed is:
1. A multi-stage Pressure Swing Adsorption process to remove contaminant gases from raw methane streams, comprising at least two Pressure Swing Adsorption stages:
 a first stage for removing Nitrogen and Oxygen, comprising the following steps:
  Feed ("FD");
  Adsorption ("AD");
  Equalization provided ("ET");
  Blowdown ("BD");
  Evacuation ("EV");
  Purge ("PG");
  Equalization received ("E↓"), wherein the first stage comprises at least one adsorbent, or mixture thereof, with strong affinity for carbon dioxide and methane;

second stage for removing Carbon Dioxide and residual Nitrogen and Oxygen comprising the following steps:
Adsorption ("AD");
Co-current depressurization ("COD");
First equalization provided ("E1↑");
Second equalization provided ("E2↑");
Evacuation ("EV");
First equalization received ("E1↓");
Idle ("ID");
Second equalization received ("E2↓");
Idle ("ID");
wherein the second stage comprises at least one adsorbent, or mixture thereof, with strong affinity for carbon dioxide.

2. The process according to claim 1, wherein the second stage further comprises a Blowdown ("BD") stage after the Second equalization provided ("E2↑") step and before the Evacuation ("EV") step.

3. The process according to claim 2, wherein the Co-current depressurization ("COD") step of the second stage occurs after the Second equalization provided ("E2↑") and before the Evacuation ("EV") step.

4. The process according to claim 1, wherein the second stage comprises a Backfill ("BF") stage after the Second equalization received ("E2↓") and before the second Idle ("ID") stage.

5. The process according to claim 1, wherein the second stage comprises a Backfill ("BF") stage after the second Idle ("ID") stage.

6. The process according to claim 1, wherein it comprises a pre-treatment step before the first stage.

7. The process according to claim 1, wherein the first stage operates at a temperature between −50° C. and 120° C.

8. The process according to claim 1, wherein the operating pressure during the adsorption step in the first stage is between 60 kPa and 1500 kPa.

9. The process according to claim 8, wherein the purge to feed ratio varies between 0.3 to 0.9 depending on nitrogen feed stream content.

10. The process according to claim 1, wherein the operating desorption pressure in the evacuation step of the first stage ranges from 1 kPa to 100 kPa.

11. The process according to claim 1, wherein an intermediate biogas stream resultant of the first stage is pressurized between 200 kPa to 4,000 kPa and fed to the adsorption beds of the second stage.

12. The process according to claim 1, wherein the second stage operates at a temperature between −50° C. to 150° C.

13. The process according to claim 1, wherein the operating pressure during the adsorption step of the second stage is between 200 kPa and 4,000 kPa.

14. The process according to claim 1, wherein the operating desorption pressure in the evacuation step of the second stage is between 0.001 kPa and 100 kPa.

15. The process according to claim 1, wherein adsorbents used in the first and second stage are selected from the group consisting of zeolites, titanosilicates, metal-organic frameworks, activated carbons, carbon molecular sieves, alumina, silica gel, ionic liquid zeolites and Si/Al-based mesoporous materials.

16. The process according to claim 1, wherein the first stage equalization occurs through the top of adsorbent vessels.

17. The process according to claim 1, wherein the first stage equalization occurs through the bottom of adsorbent vessels.

18. The process according to claim 1, wherein the desorption in the evacuation step of the second stage occurs with purge.

19. The process according to claim 1, wherein the desorption in the evacuation step of the second stage occurs without purge.

* * * * *